United States Patent [19]

Norton et al.

[11] 4,303,594
[45] Dec. 1, 1981

[54] PROCESS FOR THE PRODUCTION OF ISOBUTYRIC ACID ANHYDRIDE

[75] Inventors: Richard V. Norton; Lee R. Zehner, both of Dublin; Ralph F. Pascoe, Marysville; John E. Corn, Jr., Westerville; Dace Grote, Columbus, all of Ohio

[73] Assignee: Ashland Oil, Inc., Ashland, Ky.

[21] Appl. No.: 143,693

[22] Filed: Apr. 25, 1980

[51] Int. Cl.$^3$ ............................................. C07C 51/54
[52] U.S. Cl. .................................. 260/546; 260/544 A
[58] Field of Search ............................ 260/544 A, 546

[56] References Cited

U.S. PATENT DOCUMENTS 2,053,233 9/1936 Woodhouse .................... 260/544 A

OTHER PUBLICATIONS

Komatsu et al., Bull. Jap. Pet. Inst., 16, 124–131 (1974).

Friedman et al., J. Org. Chem. 1961, vol. 26, pp. 3751–3754.

Primary Examiner—Natalie Trousof
Assistant Examiner—Frederick W. Pepper
Attorney, Agent, or Firm—William Kammerer

[57] ABSTRACT

A process for the production of isobutyric acid anhydride in which propylene is initially carbonylated in the presence of a substantial molar excess of liquid anhydrous hydrogen fluoride to provide a reaction mixture of isobutyroyl fluoride and unreacted hydrogen fluoride. Following distillation of the reaction mixture to recover a recycle stream of hydrogen fluoride, the isobutyroyl fluoride residue is partially hydrolyzed in the presence of a hydrogen fluoride acceptor resulting in a hydrolysis product consisting essentially of isobutyroyl fluoride, isobutyric acid anhydride and a hydrogen fluoride complex of said acceptor. Following removal of the solid complex, the hydrolysis product is fractionally distilled to yield an overhead fraction of isobutyroyl fluoride for reuse in the hydrolysis reaction.

5 Claims, 1 Drawing Figure

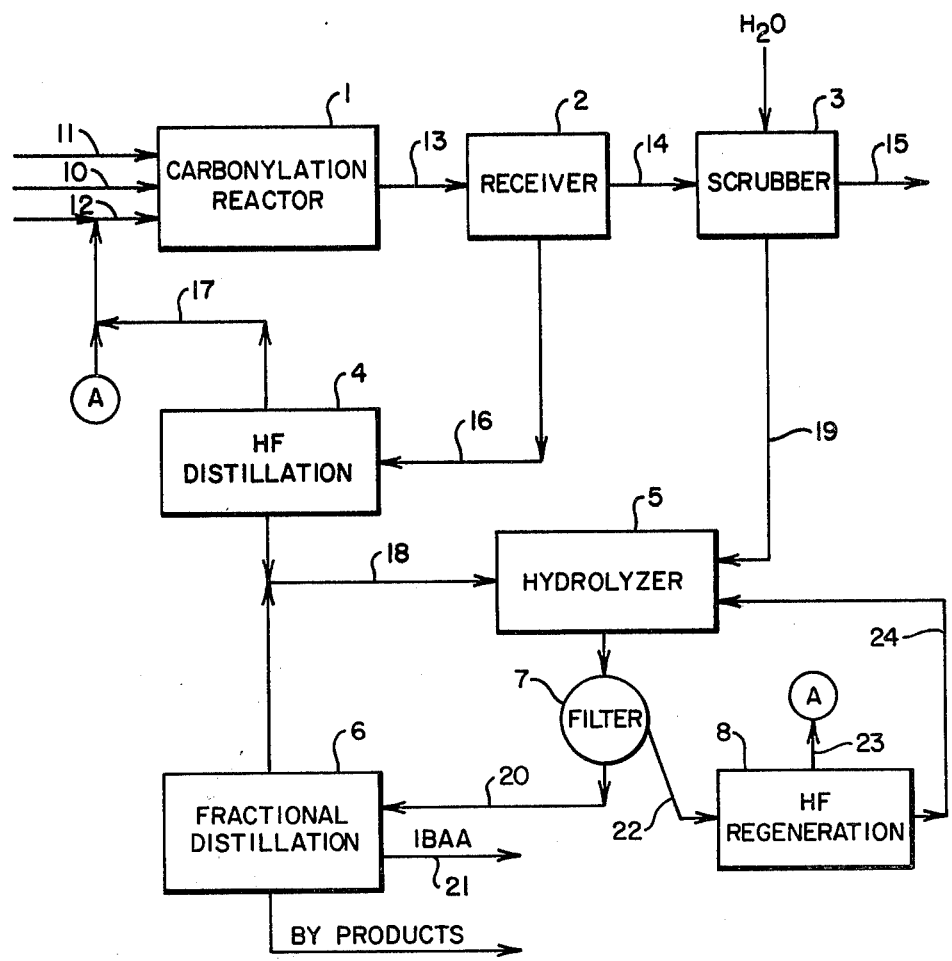

PROCESS FOR THE PRODUCTION OF ISOBUTYRIC ACID ANHYDRIDE

BACKGROUND OF THE INVENTION

1. Field of the Invention

This invention relates to a process for the production of a lower carboxylic acid anhydride from the corresponding mono-acyl fluoride.

2. Description of the Prior Art

It is known that olefins react readily with carbon monoxide at low temperatures and under moderately high pressure in the presence of a strong acidic medium, typically representative of which include anhydrous hydrogen fluoride, concentrated sulfuric acid and anhydrous chlorosulfonic acid. The postulated carbonylation mechanism involved is conventionally referred to as the Koch reaction and is exemplified in U.S. Pat. No. 2,831,877. The foremost problem faced in any commercial implementation of the Koch reaction in the production of a lower carboxylic acid resides in the difficulty experienced in recovering the acid catalyst in the form suitable for recycling.

Komatsu et al in Bull, Jap. Pet. Inst., 16 124–131 (1974) address this recovery aspect as such specifically applies to the Koch reaction employing a lower olefin. A procedure is accordingly outlined therein for the recovery of HF following preparation of pivalic acid in accordance with the Koch reaction. Essentially the procedure involves hydrolyzing the carbonylation reaction mixture with an equimolar mixture of hydrogen fluoride and water (54% aqueous HF) and distilling to recover anhydrous HF. Thereupon the residue in the form of a equimolar HF complex of pivalic acid is hydrolyzed using a minimum amount of water to provide two layers; the top layer being the carboxylic acid product and the other being recyclable 54% aqueous HF.

Unfortunately, this method is not applicable in a like process for preparing isobutyric acid insofar as the said carboxylic acid is soluble in 50% aqueous HF. The only way to effect phase separation is to dilute the carboxylic acid solution with a substantial amount of water. The net result is that a mole of HF per mole of the carboxylic acid product is effectively non-recoverable for use in the process.

SUMMARY OF THE INVENTION

In accordance with this invention an integral process is provided for the production of isobutyric acid anhydride via the Koch reaction in which liquid anhydrous HF is utilized as the reaction medium or catalyst. The gist of the invention is that of providing a method within the overall processing scheme whereby the HF can be essentially completely recovered in the anhydrous form for recycling purposes. In the initial phase of the process propylene is carbonylated in the presence of a substantial molar excess of anhydrous HF thereby converting the propylene to isobutyroyl fluoride. The unreacted HF is recovered by distillation for recycle and the residue consisting essentially of isobutyroyl fluoride is partially hydrolyzed with water in the presence of a hydrogen fluoride acceptor. The hydrolysis reaction is carried out to the extent whereby the water is used to extinction thereby providing an equilibrium mixture consisting essentially of isobutyroyl fluoride, isobutyric acid anhydride and a HF complex of said acceptor formed during the course of the hydrolysis reaction. Following removal of the solid complex, the hydrolysis product is fractionally distilled to yield an overhead isobutyroyl fluoride fraction for recycling and an intermediate fraction predominantly composed of isobutyric acid anhydride. In a further aspect of the invention, the spent acceptor is regenerated to provide anhydrous HF and acceptor for recycle.

BRIEF DESCRIPTION OF THE DRAWING

The accompanying drawing is a flow diagram schematic illustrating the production of isobutyric acid anhydride via the carbonylation of propylene in the presence of anhydrous HF wherein the method of the present invention is implemented for the internal cyclical reuse of the anhydrous HF.

DETAILED DESCRIPTION OF THE INVENTION

Although the present invention represents but a certain aspect of an overall process for producing isobutyric acid anhydride, much of which is prior art, a detailed description of the invention must necessarily be given in context of the contemplated overall processing scheme. Reference is accordingly had to the accompanying drawing which first depicts a carbonylation reactor 1 wherein anhydrous hydrogen fluoride, a petroleum grade propylene and carbon monoxide are reacted to produce isobutyroyl fluoride with essentially 100% selectivity. In this connection mention will be made of the operating conditions determined to be optimum in a particular reactor design. These conditions may or may not be optimum for a different design. However, the determination of such conditions for any particular design is within the province of a skilled worker.

The carbonylation reaction is carried out at a pressure of 340 atmospheres provided by the carbon monoxide feed stream (11) and a temperature of about 30° C. The propylene feed stream (10) is combined with the anhydrous HF stream (12) to provide a mole ratio of 1:15, respectively, within the carbonylation reactor. The residence time within the reactor is 30 minutes. The reactor effluent stream (13) is passed through adiabatic expansion valves (not shown) into the receiver or primary flash tank 2 within which the pressure is 20 atmospheres.

The off-fuel gas stream (14) from the receiver 2 is passed through scrubber 3 whereas the condensate composed mainly of isobutyroyl fluoride and liquid HF as stream (16) is introduced into the HF distillation still 4. The overhead HF fraction along with make-up HF constitutes the main HF reactor feed stream (12). The isobutyroyl fluoride residue from the HF distillation still 4 is introduced into the hydrolyzer 5 as the principal feed (18) thereto. Water is introduced into the hydrolyzer which is shown emanating from the off-fuel gas scrubber 3 as stream (19). The third feed to the hydrolyzer is the HF acceptor which in this particular exemplication is sodium fluoride as represented by stream (24).

The hydrolysis is carried out at a temperature between about 0° and 100° C. and more preferably from 0° to 40° C. in the presence of from 0.05 to 0.5 mole of water per mole of the isobutyroyl fluoride present in the hydrolysis reaction mixture and more preferably from 0.2 to 0.4 mole on the same basis. It is essential that the water be used to extinction in the course of the hydrolysis reaction. The resultant hydrolysis reaction product is an equilibrium mixture of isobutyric acid anhydride, isobutyroyl fluoride and the complexed sodium fluoride. A further feature of this invention is that of maintaining an appropriate amount of isobutyroyl fluoride in the equilibrium mixture which importantly serves as a solvent for the isobutyric acid anhydride. Upon recovery of the complexed sodium fluoride by filtration as shown or by other suitable means; e.g., centrifugation, the homogenous phase as stream (20) is introduced into the product fractional distillation column 6. The overhead fraction of isobutyroyl fluoride from column 6 is recycled to the hydrolyzer 5 and a product fraction of isobutyric acid anhydride is recovered as identified by stream (21).

While the above description refers to the use of sodium fluoride as the hydrogen fluoride acceptor, a variety of other compounds are applicable for this purpose. In the context of this invention an acceptor is broadly any compound which will accept a proton but at the same time will not competitively react with either isobutyroyl fluoride or isobutyric acid anhydride. The preferred acceptors are the alkali metal fluorides, particularly sodium fluoride exemplified herein. These salts are attractive because they readily complex with HF and are easily regenerated via a heat treatment with concurrent release of anhydrous HF. Activated carbon represents another suitable acceptor capable of being regenerated by heat. Tertiary amines, basic ion exchange resins as well as alkali metal oxides are capable of serving as acceptors. However, regeneration of the latter acceptors is not as facile as in the case of the indicated preferred acceptors.

Reverting to the accompanying drawing in connection with this discussion, the complexed sodium fluoride is shown as stream (22) from filter 7 to the HF regenerator 8. In this instance the regenerator takes the form of a simple kiln. The generated HF is shown as stream (23) which is combined with stream (17) from HF DISTILLATION 4 for recycle to the carbonylation reactor 1 along with make-up HF. The regenerated sodium fluoride (24) is accordingly recycled to the hydrolyzer 5.

EXAMPLE I

In order to illustrate the best mode contemplated for practicing the present invention, the detailed description presented above is supplemented herein by providing the compositional data of the various process streams outlined in the drawing. This data is given on the basis of a unit designed to produce about 100 lb. moles of isobutyric acid anhydride per hour. Accordingly, the flow rates (lb. moles/hr.) of the various streams are tabularly listed in the following Table 1.

TABLE I

STREAM FLOW RATES IN PRODUCTION OF ISOBUTYRIC ANHYDRIDE (LB. MOLES/HR)

| STREAM NO. | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|
| PROPYLENE | 220.0 | | | 6.6 | 6.5 | 6.3 | .1 | 23.1 | | .2 | .2 | | | | |
| PROPANE | 94.3 | | | 94.3 | 94.0 | 90.0 | .3 | .3 | | .3 | .3 | | | | |
| CARBON MONOXIDE | | | 242.0 | 28.6 | 27.7 | 27.3 | .9 | .9 | | .4 | .4 | | | | |
| HYDROGEN FLUORIDE | | | 3300 | 3086.5 | 10 | Tr | 3076.5 | 3000(−) | 10 | 18.4 | 128.4 | Tr | | 229.1 | |
| ISOBUTYRL FLUORIDE | | | | 202.7 | | | 202.7 | | 5 | 200.7 | Equil. | | | | |
| ISOBUTYRIC ACID | | | | | | | | | | 2 | Equil. | | | | |
| ISOBUTYRIC ANHYDRIDE | | | | | | | | | | | Equil. | 98.0 | | | |
| WATER | | | | | | 5.2 | | | | 101.4 | | | | | |
| HEAVY FLUORIDES | | | | 10.7 | | | 10.7 | .7 | 10 | | | | | | |
| SODIUM FLUORIDE | | | | | | | | | | | | | 229.1 | | |
| NaHF$_2$ COMPLEX | | | | | | | | | | | | | 229.1 | | |

We claim:

1. In a process for carbonylating propylene in the presence of a substantial excess of liquid anhydrous hydrogen fluoride to effect the formation of isobutyroyl fluoride followed by hydrolysis; the improvement of hydrolyzing the isobutyroyl fluoride to effect the formation of isobutyric acid anhydride and recycle anhydrous hydrogen fluoride comprising the steps:
   (1) fractionating the carbonylation reaction mixture to provide unreacted anhydrous hydrogen fluoride for recycle and isobutyroyl fluoride;
   (2) partially hydrolyzing the isobutyroyl fluoride at a temperature between about 0° and 100° C. in the presence of a hydrogen fluoride acceptor and from 0.05 to 0.5 mole of water per mole of the isobutyroyl fluoride whereby the water is used to extinction in the hydrolysis reaction thereby providing an equilibrium hydrolysis reaction mixture including a liquid phase consisting essentially of isobutyroyl fluoride and isobutyric acid anhydride and a solid phase consisting of a hydrogen fluoride complex of said acceptor;
   (3) fractionally distilling said liquid phase of the hydrolysis reaction mixture to provide an overhead fraction of isobutyroyl fluoride for recycle to said hydrolysis step (2) and an isobutyric acid anhydride product fraction.

2. A process according to claim 1 wherein said hydrolysis step (2) is effected at a temperature between 0° and 40° C. and in the presence of from 0.2 to 0.4 mole of water per mole of isobutyroyl fluoride.

3. A process according to claim 2 wherein said hydrogen fluoride acceptor is an alkali metal fluoride.

4. A process according to claim 3 wherein said acceptor is sodium fluoride.

5. A process according to claim 3 or 4 wherein the hydrogen fluoride complexed acceptor is recovered from the hydrolysis reaction mixture of step (2) and heated to provide recycle anhydrous hydrogen fluoride and regenerated acceptor for reuse in the hydrolysis step (3).

* * * * *

UNITED STATES PATENT AND TRADEMARK OFFICE
CERTIFICATE OF CORRECTION

PATENT NO. : 4,303,594

DATED : December 1, 1981

INVENTOR(S) : Richard V. Norton; Lee R. Zehner; Ralph F. Pascoe; John E. Corn, Jr.; and Dace Grote It is certified that error appears in the above-identified patent and that said Letters Patent are hereby corrected as shown below:

Under Columns 3 and 4 in TABLE I under the item "Sodium Fluoride" the Stream Flow Rate (229.1) should be under Stream No. 24 instead of Stream No. 23.

Signed and Sealed this

Thirty-first Day of August 1982

[SEAL]

Attest:

*Attesting Officer*

GERALD J. MOSSINGHOFF

*Commissioner of Patents and Trademarks*